United States Patent
Loginov

(10) Patent No.: US 7,362,109 B2
(45) Date of Patent: Apr. 22, 2008

(54) GEM TESTER USING ELECTRICAL PHOTOCONDUCTIVITY

(76) Inventor: Boris Zolotar Loginov, 5565 La Jolla Mesa Dr., La Jolla, CA (US) 92037

( * ) Notice: Subject to any disclaimer, the term of this patent is extended or adjusted under 35 U.S.C. 154(b) by 0 days.

(21) Appl. No.: 11/252,686

(22) Filed: Oct. 18, 2005

(65) Prior Publication Data

US 2006/0087306 A1    Apr. 27, 2006

Related U.S. Application Data

(60) Provisional application No. 60/619,576, filed on Oct. 18, 2004.

(51) Int. Cl.
*G01R 27/08* (2006.01)
(52) U.S. Cl. .............. 324/693; 324/71.1; 324/691; 324/713; 324/717; 324/722
(58) Field of Classification Search ........... 324/717, 324/71.1, 693, 722, 691, 705, 713, 715; 374/44
See application file for complete search history.

(56) References Cited

U.S. PATENT DOCUMENTS

| | | | | |
|---|---|---|---|---|
| 2,789,430 A | * | 4/1957 | Sinclaire ............... 73/161 |
| 4,255,962 A | * | 3/1981 | Ashman ............... 374/10 |
| 4,344,315 A | * | 8/1982 | Moxon et al. .......... 374/44 |
| 4,364,677 A | * | 12/1982 | Ashman ............... 374/44 |
| 4,394,580 A | * | 7/1983 | Gielisse ............ 250/461.1 |
| 4,488,821 A | * | 12/1984 | Wenckus ............. 374/44 |
| 5,801,819 A | * | 9/1998 | Spear et al. ........... 356/30 |
| 5,883,389 A | * | 3/1999 | Spear et al. ........ 250/461.1 |
| 5,955,735 A | | 9/1999 | Coleman |
| 6,265,884 B1 | * | 7/2001 | Menashi et al. ....... 324/717 |
| 6,439,766 B1 | * | 8/2002 | Nelson ............... 374/44 |
| 7,126,351 B2 | * | 10/2006 | Claus ................ 324/663 |

\* cited by examiner

*Primary Examiner*—Andrew H Hirshfeld
*Assistant Examiner*—Thomas Valone

(57) ABSTRACT

Diamond look-alikes like cubic zirconium, moissanite and other synthetic stones, are distinguishable from nature diamonds based on their thermal and/or electrical conductivities. Germ testers that are on the market are capable of evaluating these two parameters as is the present invention. Electrical resistance of moissanites reaches hundreds of thousands megohms. Existing gem esters use test voltage of 1000 volts, to be able to detect electrical conductivity in most moissanites. Still, reliable detection of high resistance moissanites is difficult. Proposed invention uses significant photo conductivity of moissanites, which was observed by the inventors, to facilitate measurement of electrical conductivity in the toughest gems, to reduce test voltage applied to gems to 300 volts, and to limit electrical test current through a gem to no more than a few micro-amps. Other refinements include: (1) multistep evaluation of electrical conductivity, which avoids applying excessive or unnecessary test voltage and current to a gem, (2) circuit design, which efficiently attenuates AC noise, (3) signal processing, which eliminates industrial pick-up, (4) usage of reference temperature sensor, which improves sensibility and repeatability of thermal measurements.

19 Claims, 3 Drawing Sheets

GEM TESTER USING ELECTRICAL PHOTOCONDUCTIVITY

RELATED APPLICATION

This application claims the benefit of U.S. Provisional Application Ser. No. 60/619,576 filed on Oct. 18, 2004 entitled "Using Electrical Photoconductivity to Distinguish High-resistance Moissanites from Natural Diamonds," the entire teachings of which are herein incorporated by reference.

BACKGROUND OF THE INVENTION

The old task of distinguishing diamonds look-alikes from natural diamonds continues to be important. However this task becomes ever more difficult as quality of synthetic gems, which are partially indistinguishable from natural diamonds with the naked eye, improves and their characteristics, which could be used for the purpose of distinguishing them from natural diamonds, approach those of natural diamonds.

Two techniques, which are usually used in portable diamond testers, are based on diamonds' exceptionally high thermal conductivity and their high electrical insulation ability. Those diamond look-alikes that have similar electrical insulation ability, such as cubic zirconium, have low thermal conductivity, while those, which have thermal conductivity close to that of diamond, such as silicon carbide popularly known as moissanite, are not such good insulators. Therefore, successful diamond testers combine these two techniques for reliable detection of a wider spectrum of look-alike gemstones.

As technology progresses, moissanites with even smaller electrical conductivity are becoming available. There are gems on the market with electrical resistance in excess of 100,000 Megohms. Discriminating such weak conductors from a good insulator, like diamond, using a portable battery operated device is difficult, and even the best available testers cannot do it reliably.

It has been noticed that electrical conductivity of a moissanite gem can vary widely and even may be affected by the electrical current that passes through the gem during previous tests. Consequently, for a reliable test result it is desirable to subject the gem under test to as little and as short electrical disturbance as possible.

In order to be able to do measurements of the objects with so high resistance it is necessary to increase sensitivity of the measuring instrument. This aggravates the problem of picked AC interference, which depends on the environment and is practically unavoidable when such instrument contacts electrically with body of the user. So, while useful measurement signal for highly resistive gems goes down, interfering AC signal may become a dominating part of the signal if the measuring circuit is not designed carefully and/or adequate signal processing is not implemented.

Applying up to a 1000 V indiscriminately to a gem under test, as it is done in existing diamond testers, is not always necessary and can be counterproductive. There is also an issue of operator's safety and comfort if the operator's body becomes a part of the high voltage circuit, whether accidentally or by design. A possibility of unpleasant, let alone harmful, electrical shock under any scenario must be eliminated.

SUMMARY OF THE INVENTION

The present invention addresses above-mentioned difficulties and issues by providing a method and apparatus for reliable detection of a wider variety of natural diamond look-alikes.

In order to be able to diagnose most of diamond look-alikes, namely those that exhibit diamond-like thermal conductivity as well as those that are good electrical insulators, our device combines the means for evaluation of thermal conductivity and also circuitry for measuring electrical conductivity.

Thermal conductivity is estimated by the speed at which preheated copper probe cools down when it touches the object under test. The cooling process is affected by many causes, some of which cannot be controlled or easily accounted for. To achieve reliable estimate of thermal conductivity in presence of unknown factors we used differential method by employing two temperature sensors. One, measurement sensor, which is closer to the tested object, is used for sensing the effects caused by the tested object while the other, reference sensor, which is separated from the tested object by the heating element, accounts for all other influences. The reference signal is subtracted from the measurement signal resulting in more robust and reproducible estimates.

Another problem associated with thermal measurements using hot probe is the time, which is required to preheat the probe. This delay every time the device is turned on is annoying and counterproductive. By using microprocessor for managing the heating circuitry we were able to reduce this time to 2-3 seconds.

The electrical portion was modified and upgraded to meet increasing challenge and to provide better reliability, productivity, safety, and convenience.

Moissanites exhibit quite a wide range of electrical conductivity. Besides, conductivity of the same stone may vary widely from test to test. Sometimes it may be difficult to tell a moissanite gem from 'short' circuit, which means that electrical resistance of the stone is no more than a few megohms. On the other end the toughest moissanites may have resistance approaching a tera-ohm, or a million megohms.

Our observations demonstrated that moissanites possess significant photoconductivity, which means that electrical current caused by applying voltage across the stone increases sharply when the stone is exposed to sufficiently bright light of sufficiently short wavelength. While this effect may be difficult to notice in better conducting stones, in the high-resistance stones, which have small electrical conductivity, the photocurrent becomes the dominant part of electrical current. We incorporated in our device a high intensity white light emitting diode (LED), which is placed in the tip above the probe. This LED is turned on when no significant 'dark' electrical conductivity is found. This expands significantly the range of diamond look-alikes that can be detected.

In order to cover a wide range of electrical resistance a two-stage electrical conductivity test is performed. First, normal battery voltage is applied to determine if there is a short circuit between the probe and high voltage. This test also determines synthetic gems with resistance below 100 megohms. In such case no further testing is needed. Only if resistance is found to be large enough the high voltage generator is activated and light exposure is used. High voltage builds up in milliseconds because the load is small.

It is applied for 0.15 sec, the time necessary for the test voltage to settle and for the processor to filter out possible AC interference.

Range of the instrument was further increased by using amplifier with gain of 10 in addition to usual amplifier with gain of 1. The microprocessor checks the low gain signal before turning to the high gain output.

As the result of all described measures we were able to reduce the high voltage down to 300 volts. No more than about 300 volts is required to be applied to distinguish diamond look-alike gems, such as high resistance moissanites, from natural diamonds.

Test voltage is connected to the gem under test through the operator's body by means of special contact pad on the device case, which is touched by the operator's finger. Initially, the test voltage is about 5 volts and poses no threat or inconvenience thanks to the current limiting resistor of a few megohms, resulting in electrical current less than 1 micro-amp. The high voltage is turned on when resistance of the gem is high enough. In this case operator's body, which has electrical resistance anywhere between several kilohms and a few megohms and is in series with a gem having at least hundreds of megohms, is subjected to a harmless portion of the test voltage and to a minuscule electrical current.

In summary, our invention uses the lowest test voltage for the least time, resulting in minimal effect on the objects being tested, better safety and comfort for the user, and smaller power consumption.

Measurement circuit from the source of the test voltage goes through the operator's body, then through the metal of the ring or the test plate, then through the gem to the probe, which is connected to the amplifier input. AC interference enters the circuit from the operator's body, in the described measurement circuit the interference signal is divided in the same proportion as the test voltage in the resistive divider, which includes the gem under test. This prevents the interference signal from becoming a dominant component of the small test signal when dealing with high resistance gems.

To further reduce the error caused by AC interference, measured signal is rid of industrial pick up, which normally is the main part of the interference. This is achieved by averaging a sufficient number of evenly distributed samples over 0.1 sec. This time interval contains a whole number of cycles of 50, 60, 100, and 120 Hz, which are the frequencies of industrial AC and of rectified power voltage in different countries. Averaging over whole number of cycles of a periodic signal results in removal of the periodic components below alias frequency.

All measurements are conducted under control of a microprocessor, which also maintains operating condition of the device.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

As other successful diamond testers on the market, present invention employs both thermal and electrical conductivity testing for the purpose of determining reliably whether the stone being testied is a natural diamond.

It should be noted that this device does not actually establish if the object, which is being tested, is a diamond, a moissanite, a synthetic diamond, or, say, cubic zirconium. Such positive identifications would require more sophisticated equipment and longer testing. The device just evaluates thermal and electrical conductivities. By the results of these measurements tested objects are determined as following. Those with electrical conductivity above certain threshold are announced as metal. Those with thermal conductivity below certain threshold are diagnosed as simulants. These may include cubic zirconium, some synthetic gems, plastics, or glass. Those with high thermal conductivity are diagnosed as diamonds when electrical conductivity is below certain threshold or as moissanites otherwise.

Figure 1:
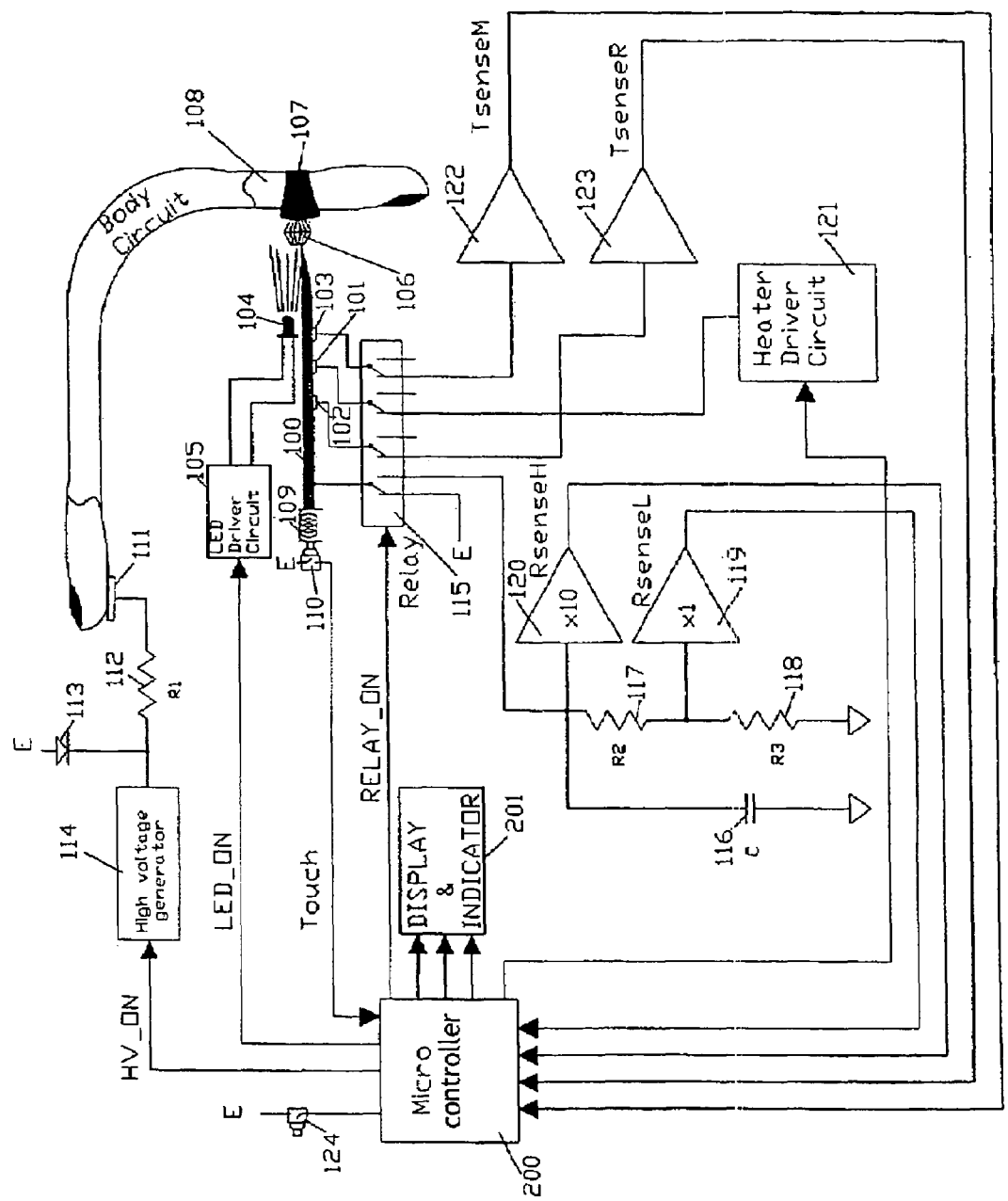
FIG. 1 shows the principle and major features of the apparatus for distinguishing diamond look-alikes from natural diamonds with the help of photoconductivity.

Refer diagram of the invention presented in FIG. 1.

Operation of the device is managed by the micro-controller 200 (MCU). Modern micro-controllers combine analog and digital circuitry and can work with digital as well as analog signals. The diagram shows analog signals connected to MCU 200. These signals are converted to digital form by its internal analog-to-digital converter.

The device is built around the sensor 100, which is a copper rod. The copper rod performs two functions. During thermal conductivity evaluations it serves as a heat probe. When electrical conductivity is being evaluated the rod serves as conductor of the test signal from the gem. Which of the two functions is performed depends on condition of the 4-pole double throw relay 115 controlled by MCU 200 via digital control signal 'RelayON'. When this signal is low, relay 115 is not active and the circuitry is configured for thermal conductivity measurement through its normally closed contacts. When the signal 'RelayON' is high device is configured for measuring resistance.

The hardware for thermal conductivity testing consists of the following. The rod itself serves as the heat conductor as well as a wire for the heater current. As such, it is connected to one of the 4 poles of relay 115, which is normally connected to the battery, from which heater gets its power. Mounted on the copper rod is heating resistor 101, reference thermistor 102, and measuring thermistor 103. Measuring thermistor 103 is placed closer to the sensing end of the rod 100, while reference thermistor 102 is placed on the other side of the heating resistor 101. The heating resistor 101 and thermistors 102 and 103 are wired to the remaining three poles of the relay 115. For thermal operation they are connected through normally closed contacts of the relay 115 as follows: thermistors are connected to their respective amplifiers', 123 and 122, inputs and the heating resistor is connected to the heater driving circuit 121. Amplifier 122 produces analog signal 'TsenseM', amplifier 123 produces analog signal, 'TsenseR'. Digital signal from MCU 200 'HeaterON' controls heater driving circuit 121. When 'HeaterON' is high, electrical current is sent through heating resistor 101.

Normally, test is initiated when heated probe touches a cold surface. This causes the probe to cool down which affects 'TsenseM' signal and thus is detected by MCU 200, which starts the test sequence. Sometimes, when thermal conductivity is very low the touch cannot be sensed this way. In such cases the test is started by the signal 'Touch' from switch 110, which is activated by motion of probe 100 through the spring 109. However, switch 110 cannot be relied upon to start testing in all cases because mechanical delay, which can change signficantly from one user to another, produces unpredictable error in estimating the speed of cooling, by which diamonds are detected.

To carry out electrical conductivity measurement, relay 115 must be active, that is MCU 200 control signal 'RelayON' must be high. Copper rod 100 then is connected to resistance measurement circuit, which consists of capacitor 116 for filtering out high frequency interference, resistors 117, 118 forming a divider, and amplifiers 119, 120. Amplifier 119, which has gain of 1, produces analog output signal 'RsenseL' and Amplifier 120, which has gain of 10, produces analog output signal 'RsenseH'. Connections to heater 101 and to thermistors 102 and 103 are open. Copper rod 100 serves as a path for the test current. The test circuit includes high voltage generator 114, which is turned on when control signal 'HvoltON' from micro-controller 200 is high. When generator of high voltage 114 is turned off, the test voltage comes from the battery through diode 113. The test voltage is connected to conductive pad 111 via current limiting resistor 112. Conductive pad 111 is placed on the device casing to be touched by the hand holding the device. Measurement circuit is closed through the operator's body 108, the ring 107 the gem 106, and on to the probe 100 touching the gem.

Close to the sensing end of the rod 100 is mounted an ultra-bright white light emitting diode (LED) 104, which is wired to the LED driver circuit 105, which is controlled by digital signal 'LightON' from MCU 200. During testing LED 104 is turned on briefly to help with detection of high resistance diamond look-alikes. By means of button switch 124, LED 104 can be turned on and off by the operator at any time and used for as long as necessary as a gem inspection hand light.

The hardware includes the circuitry for signaling about condition of the device, reporting about progress of the test procedure, and displaying the result. The indicators and displays must be adjusted for the needs of a particular market and user, and may depend on available technology and possibilities of the manufacturer. However this portion of the hardware is not claimed as an invention and does not constitute an essential part of this invention.

Figure 2A:
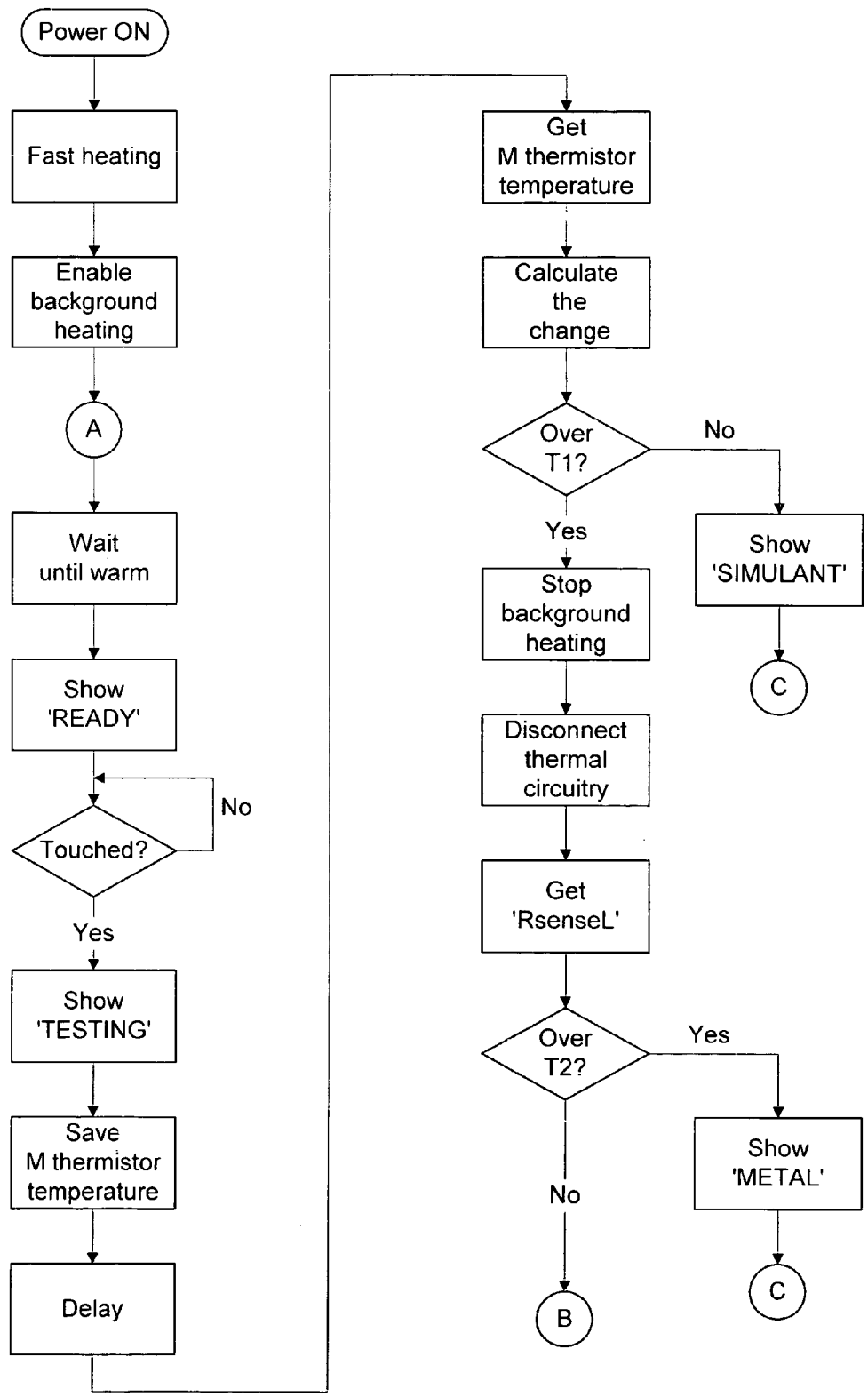
FIGS. 2A, 2B present the flowchart illustrating measurement methodology.
Figure 2B:
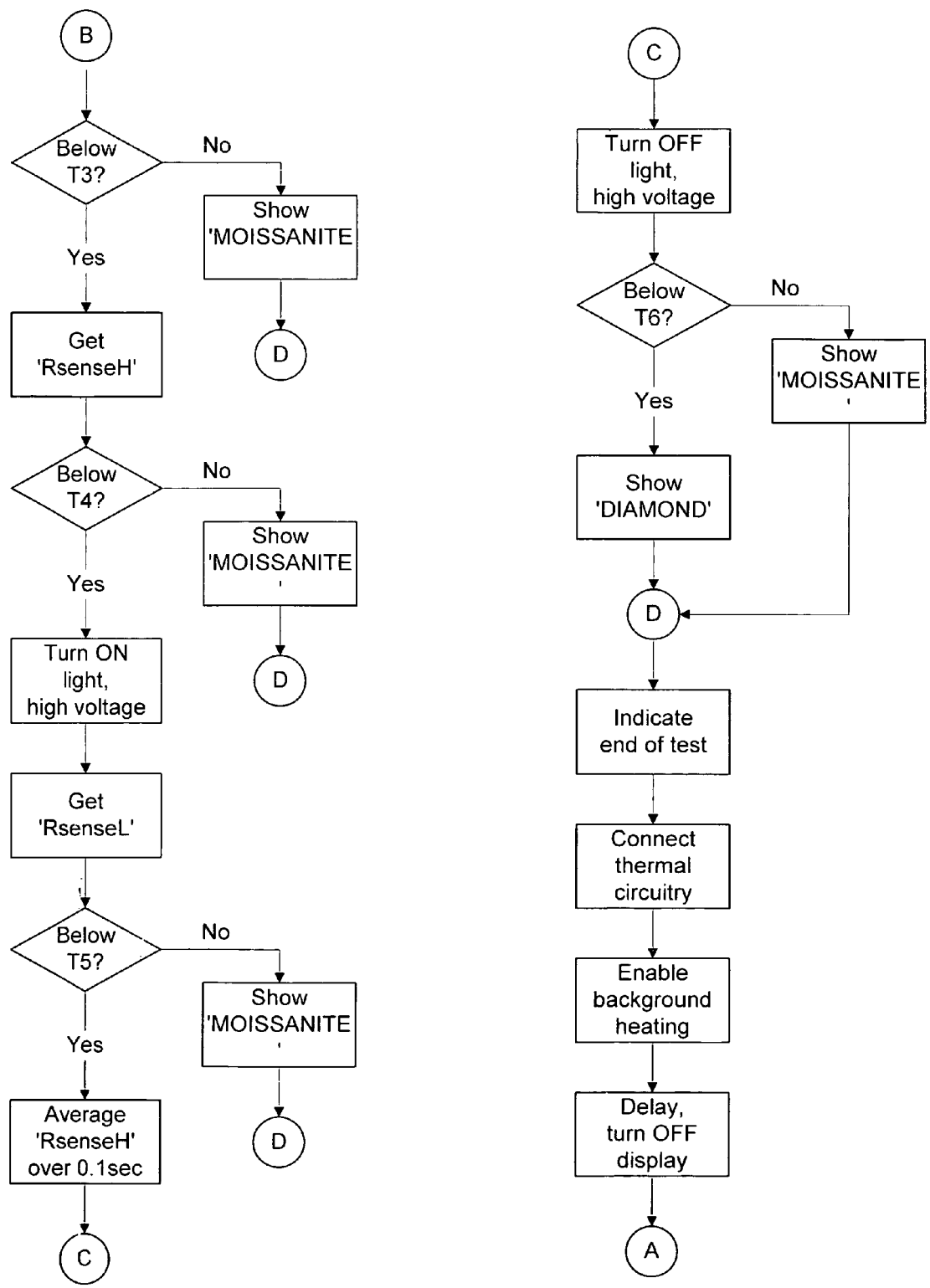

Measurement technology and device operation are better understood with the help of flowchart presented in FIGS. 2A, 2B.

After device is turned on, it is configured for thermal measurement by default. MCU 200 uses fast heating routine to heat up sensor 100 near working temperature in 2-3 seconds. After that a background heating activity is started and enabled, which is driven by interrupt from the MCU internal timer. This background process gently brings temperature of reference thermistor 102 to working level and maintains it there by regularly checking signal 'TsenseR' from reference thermistor. After enabling the background process, the MCU waits until temperature of reference thermistor hits the target and then indicates that device is ready to be used for testing. Then MCU watches the signal 'TsenseM' from measurement thermistor 103 and signal 'Touch' from the tip switch 110. Signal 'TsenseM' indicates that the probe 100 touched cold surface which has sufficient thermal conductivity. Depending on how strongly and quickly user of the device touches the gem, this signal may be followed by 'Touch' signal after somewhat uncertain time interval. However, after thermal detection of a touch the mechanical signal 'Touch' is ignored and its uncertainty does not affect the measurement. On the other hand, if the tested gem has very low thermal conductivity, frustrated user will have to press the probe hard enough to produce the mechanical signal to the MCU in order to get response from the device. Cooling of measurement thermistor 103 in this scenario is hardly noticeable and timing uncertainty of the mechanical signal is inconsequential: the gem will be diagnosed as a 'simulant', a term for diamond substitutes with low thermal conductivity.

After detecting a touch, MCU starts the measurement cycle. Value of 'TsenseM' at the start of the test is saved. Now it must be said about dual role of reference thermistor 102. It was explained already how it is used for maintaining working temperature of probe 100 while temperature of the measurement thermistor monitors condition at the probe's tip. Another very essential role of the reference thermistor is that for all thermal measurements MCU always uses difference of the signals from two thermistors, namely 'TsenseM', 'TsenseR'. Signal 'TsenseM' is affected by many factors in addition to thermal conductivity of the touched surface. Trying to control all these factors or to take them into consideration would be impractical. By subtracting signal from the reference thermistor we can compensate for such uncertainties as parameters of the heater, variations of the power source voltage, and noise on the power line, to name a few.

After about 0.1 sec delay 'TsenseM' from the measurement thermistor 103 is evaluated again and previous value of this signal is subtracted in order to establish the speed of cooling. The result is saved and compared to threshold T1, representing the limit, below which a gem is considered 'simulatn'. If such is the case, MCU indicates 'SIMULANT', skips the remainder of test procedure and proceeds to the test recovery stage.

Otherwise, MCU disables the background heating process and reconfigures the circuitry for resistance measurements by pulling high the 'RelayON' signal and thus activating the relay 115. The probe 100 is now disconnected from the battery, from heater driving circuit, and from thermistor amplifiers. The only connections now are: (1) from the probe to resistance measurement circuit, and (2) to the test voltage through the stone 106, ring 107, operator's body 108, the test voltage pad 111, and current limiting resistor 112. The test voltage at this time is equal to the device battery voltage. Electrical current through the measurement circuit and through the operator's body is less than one micro-amp even with a short circuit. After delaying for amount of time needed for relay 115 to complete switching. MCU checks the signal 'RsenseL' and compares it to a threshold T2, above which the conductor between the operator's body 108 and the probe 100 is determined as a short circuit. If the signal exceeds the threshold, MCU indicates that the object is metal, skips the remainder of test procedure and proceeds to the test recovery stage.

Remaining portion of the procedure establishes if the gem is good enough insulator to be classified as diamond. Otherwise it is determined as moissanite. In order to prevent unnecessary excessive electrical current through the tested object and through the operator's body this is done in two stages. While the test voltage is still low, signals 'RsenseL' and later 'RsenseH' are evaluated. If sufficient electrical conductivity is detected, MCU indicates that the object is moissanite, skips the remainder of test procedure and proceeds to the test recovery stage. If no electrical conductivity is detected, MCU enters the final stage of the test. Only now high voltage generator 114 is turned on by pulling high digital control signal 'HVON'. The high voltage builds up in milliseconds because the load is definitely low. MCU also turns on LED 104, which exposes tested gem to bright white light. After a short delay to allow the test voltage to settle, 'RsenseL' and later 'RsenseH' are evaluated once more. If 'RsenseL' is still too low, it means that we are dealing with a tough gem. In this case, 'RsenseH' signal is typically small, and special technique is used to evaluate it reliably. 'RsenseH' is averaged over 0.1 sec interval. The purpose it to get rid of possible industrial pickup. Depending on the country, industrial interference is 60 and 120 Hz, or 50 and 100 Hz. Periodic signals are removed efficiently by averaging over whole number of cycles when sampling rate is no less then two per cycle of the highest harmonic. There may be 6, 12, 5, or 10 cycles of signals of concern in 0.1 sec interval depending on the local industrial frequency. Minimum number of samples for successful removal of any of the possible pickups is 24 (12 times 2). Any number over 24 of equally spaced samples accomplishes the task of ridding the measurement of these components. If electrical conductivity is detected, MCU indicates that the object is moissanite, otherwise, if no electrical conductivity is detected, MCU indicates that the object is diamond. Once the decision is made the high voltage generator and the LED are turned off, and MCU proceeds to the test recovery stage.

In the test recovery stage MCU signals end of test, reconfigures device for thermal operation, and enables the background heating process. It keeps the indicators showing the result for a second, then turns them off, indicates that device is ready for next test, and returns to the touch waiting stage.

The invention claimed is:

1. An apparatus for testing and distinguishing diamonds and diamond look-alike gems based on their electrical photoconductivity comprising:
    an electrically conductive probe adapted to contact a gem to be tested;
    a light source positioned to illuminate the gem to be tested while the probe contacts the gem and stimulates an electrical photoconductivity response in the gem;
    a generator of test voltage that stimulates electrical current through the illuminated gem, wherein no more than 300 volts is required to be applied; and
    an electronic circuit connected to the probe, the circuit comprising means for converting the electrical current flowing through the tested gem into voltage and means for processing and monitoring said voltage to evaluate electrical conductivity of the gem.

2. The apparatus of claim 1 further comprising a switch activated by contact and pressure between the probe and the gem to be tested, wherein the switch initiates testing when the probe is pressed against the gem.

3. The apparatus of claim 1 further comprising a conductive pad.

4. The apparatus of claim 3 wherein the voltage generator is connected to the conductive pad through a current limiting resistor for providing a test voltage.

5. An apparatus of claim 1 further comprising a light switch for turning the light source on and off.

6. An apparatus of claim 1 further comprising a microcontroller for carrying out the measurement of electrical conductivity and processing and monitoring the results of such measurement.

7. The apparatus of claim 1 further comprising means for measurement of thermal conductivity of the gem to be tested.

8. The apparatus of claim 7 wherein means for measurement of thermal conductivity comprises means for heating the probe and means for monitoring temperature of the heated probe.

9. The apparatus of claim 1 comprising at least one temperature sensor for measurement of thermal conductivity of the gem to be tested.

10. A method for testing and distinguishing diamonds and diamond look-alike gems based on their electrical photoconductivity comprising the following steps:
    providing an electrically conductive probe adapted to contact a gem to be tested;
    illuminating the gem to be tested with a light source to stimulate an electrical photoconductivity response in the gem;
    applying test voltage to the illuminated gem to produce electrical current through the gem, wherein no more than 300 volts is required to be applied;
    converting the electrical current flowing through the gem into voltage, processing and monitoring the converted voltage to evaluate electrical conductivity of the gem.

11. The method of claim 10 wherein the testing is initiated by using a switch activated by contact and pressure between the probe and the gem to be tested.

12. The method of claim 10 further comprising measuring thermal conductivity of the gem to be tested.

13. The method of claim 12 further heating the probe to evaluate thermal conductivity of the gem.

14. The method of claim 12 wherein thermal conductivity is evaluated by a rate at which temperature of the probe is going down as a result of touching the tested gem.

15. The method of claim 13 wherein measuring thermal conductivity is carried out with two temperature sensors wherein second temperature sensor is used to compensate for unknown and uncontrolled factors.

16. The method of claims 12 wherein electrical conductivity and thermal conductivity are measured and evaluated in sequence until it can be determined conclusively that the gem is a natural diamond or one of diamond look-alikes.

17. The method of claim 10 wherein steps of processing and monitoring are carried out under supervision of a micro-controller.

18. The method of claim 10 wherein applying test voltage is carried out with low voltage of up to 5 volts first and only if no significant conductivity is detected under low voltage, then electrical conductivity is evaluated again with test voltage up to 300 volts.

19. A method for testing and distinguishing diamonds and diamond look-alike gems based on their electrical photoconductivity comprising the following steps:
    providing an electrically conductive probe adapted to contact a gem to be tested;
    illuminating the gem to be tested with a light source to stimulate an electrical photoconductivity response in the gem;
    applying test voltage to the illuminated gem to produce electrical current through the gem, wherein applying test voltage is carried out with low voltage of up to 5 volts first and only if no significant conductivity is detected under low voltage, then electrical conductivity is evaluated again with test voltage up to 300 volts;
    converting the electrical current flowing through the gem into voltage, processing and monitoring the converted voltage to evaluate electrical conductivity of the gem.

* * * * *